United States Patent [19]
Dudasik et al.

[11] Patent Number: 5,658,351
[45] Date of Patent: Aug. 19, 1997

[54] INTRAMEDULLARY CENTRALIZER

[75] Inventors: Michael W. Dudasik, Nutley, N.J.; Kenneth Krackow, Williamsville, N.Y.; Philip C. Noble, Houston, Tex.

[73] Assignee: Howmedica Inc., New York, N.Y.

[21] Appl. No.: 510,045

[22] Filed: Jul. 31, 1995

[51] Int. Cl.⁶ ............................................ A61F 2/36
[52] U.S. Cl. .................................... 623/23; 606/95
[58] Field of Search ........................ 623/19, 23, 18, 623/22; 606/62, 67, 95

[56] References Cited

U.S. PATENT DOCUMENTS

| | | | |
|---|---|---|---|
| 3,793,650 | 2/1974 | Ling et al. | 623/18 |
| 4,245,359 | 1/1981 | Stuhmer | 606/95 |
| 4,262,665 | 4/1981 | Roalstad et al. | 606/62 |
| 4,447,915 | 5/1984 | Weber | 606/95 |
| 5,030,234 | 7/1991 | Pappas et al. | 623/23 |
| 5,092,892 | 3/1992 | Ashby | 623/16 |
| 5,171,243 | 12/1992 | Kashuba et al. | 606/86 |
| 5,470,336 | 11/1995 | Ling et al. | 606/105 |
| 5,507,831 | 4/1996 | Burke | 623/23 |
| 5,554,192 | 9/1996 | Crowninshield | 623/16 |

FOREIGN PATENT DOCUMENTS

| | | | |
|---|---|---|---|
| 0006408 | 1/1980 | European Pat. Off. | 606/95 |
| 2697430 | 5/1994 | France | 623/18 |
| 2153233 | 8/1985 | United Kingdom . | |

*Primary Examiner*—David H. Willse
*Attorney, Agent, or Firm*—Peter C. Richardson; Lawrence C. Akers; Raymond W. Augustin

[57] ABSTRACT

A centralizer for the stem of a cementable prosthetic orthopedic implant that is implanted into the medullary canal of a bone has a hollow annular body with a tapered interior surface for receiving a tapered stem of the implant. The centralizer has four fins spaced around the exterior surface of its annular body with the fins extending radially outwardly in a direction generally perpendicular to the longitudinal axis extending along the stem in a proximal-distal direction. The annular body of the centralizer has a proximal and a distal end surface spaced a predetermined distance apart with the fins having a base adjacent the body extending over a substantial portion of the predetermined distance. Adjacent fins are offset from neighboring fins in a proximal-distal direction so that when the proximal-distal dimension of the annular body is maintained, it generates a wavelike structure for the centralizer body.

20 Claims, 4 Drawing Sheets

INTRAMEDULLARY CENTRALIZER

BACKGROUND OF THE INVENTION

1. Field of the Invention

This invention relates to a distal centralizer for the stem of an intramedullary prosthesis such as a femoral implant. More particularly, it relates to a distal centralizer having four elements extending outwardly therefrom in a direction generally perpendicular to the stem with neighboring fins being offset from one another in the proximal distal direction.

2. Description of the Prior Art

Distal centralizers are used to locate the stem of a cementable prosthetic orthopedic implant in a neutral position within the medullary canal of a bone. This allows for the formation of a uniform bone cement mantle between the implant and the bone.

In general, prior art centralizers have been formed as tapered rings with fins around their periphery extending radially outwardly therefrom. The centralizer is placed over the tip of the stem and slid along a tapered portion of the stem. Usually fixation to the stem is accomplished by forming a matching taper on the inner surface of the centralizer corresponding to the taper on the stem.

Centralizers for example, as shown in British Patent Application 2 104 391 are used to centralize the distal stem in the femoral canal. Another centralizing device using vertically extending elements is shown in U.S. Pat. No. 3,793,650, which issued to the inventors of U.S. patent application 2,104,391. A polyethylene sleeve is shown in the Exeter Universal Hip system and is similar to that of 3,793,650 in that the spring elements extend vertically. It will be appreciated that these spacers are not only intended to centralize the distal tip of the prosthesis, but also to prevent the stem from actually engaging the wall of the canal.

A disadvantage with some of the prior art devices is that, when used in cemented applications, they tend to accumulate voids and air bubbles in the cement behind them as they are pushed downwardly; these voids and air bubbles form behind the fins, that is, between the fins and the metal stem of the prosthesis. This is to be avoided as it can become a point of weakness and crack initiation within the cement mantle.

Polymethylmethacrylate sleeves are known and have been taught by Leo A. Whiteside et al. in an article published in June 1988 entitled "The Effects of the Collar on Total Hip Femoral Component Subsidence" and sold as the Whiteside Total Hip System. However, this device is merely a cylindrical sleeve which can only centralize the distal stem in a precisely reamed canal.

The design of the present invention has four fins equally spaced around the periphery of the ring body of the centralizer. This enhances the ability of the centralizer to centralize in a non-circular intramedullary canal. While a greater number of fins could further increase the centralization potential of the centralizer, such a design can choke off the flow of cement around the fins upon insertion of the stem with the centralizer mounted thereon into the canal.

In addition to the fins being equally spaced, opposing pairs of the four fins are offset from one another in the proximal-distal (i.e., longitudinal) direction. This offsetting of the fins promotes in the spreading out of any discontinuities in the fresh cement beyond a single plane. The probability of crack propagation across the cement mantle in one plane is thereby reduced. It has also been found that the angle between the long axis of the stem and the leading edge of each of the attached centralizer fins should be 135° or greater, which reduces the number of cement defects caused by insertion of the component due to optimized flow dynamics. It has likewise been found that the trailing edge of each fin should be less than 90° to the long axis of the femoral component to reduce defects in the mantle. As a result of the fin pairs being offset from one another and the ring being of constant length, the tapered ring takes on a wavelike form. Thus, if sectioned longitudinally, the proximal-distal dimension of the ring remains constant giving the wavelike structure. It has been found that this distance between distal and proximal ends of the centralizer should be a maximum of 10 mm. Beyond 10 mm the rejoining of the cement flow over and beneath the ring is difficult to attain during insertion into the femoral canal. This is especially the case when the centralizer is used with a stem having grooves or depressions formed therein which allow the cement to flow both over and under the centralizer.

SUMMARY OF THE INVENTION

It is an object of the invention to provide a centralizer having improved abilities to centralize a stem intended for cemented use in a medullary canal.

It is yet a further object of the invention to provide a centralizer that consistently produces a void-free cement mantle in the area of the centralizer and the tip of the stem.

These and other objects are accomplished by a centralizer form of a ring-like hollow annular body having an interior surface for receiving the stem of an implant. The centralizer has at least three and preferably four fins spaced around the exterior surface of the annular body with said fins extending radially outwardly from the surface in the direction generally perpendicular to the longitudinal axis of the stem. At least one of the fins is offset from adjacent or neighboring fins in proximal-distal direction. Generally, if four fins are used the fins are equally spaced around the annular body with opposing pairs being at the same proximal-distal level, but being offset from the adjacent opposite pair.

The distance between the proximal and distal end surfaces of the ring-like annular body are spaced a predetermined distance apart. The fins have a base adjacent the annular body extending over substantial portion of the predetermined distance with the end surfaces undulating in a wavelike manner to compensate for the offset of neighboring fins in the proximal-distal direction. Thus, the distance between the proximal and distal end surfaces of the ring is constant as one moves 360° around the circumference of the annular body.

The annular body is tapered along the length thereof on moving toward the tip of the stem with the opposite fins of the four fins being located at the same proximal-distal location on the annular body. In addition, the length of the fins in the proximal-distal direction decreases on moving outwardly in a direction generally perpendicular to the longitudinal axis with the fins forming an angle of greater than 135° with the outer surface of the centralizer towards the tip of the stem and forming an angle of less than 90° with the trailing edge of the annular body of the centralizer, i.e.., the end away from the stem tip.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
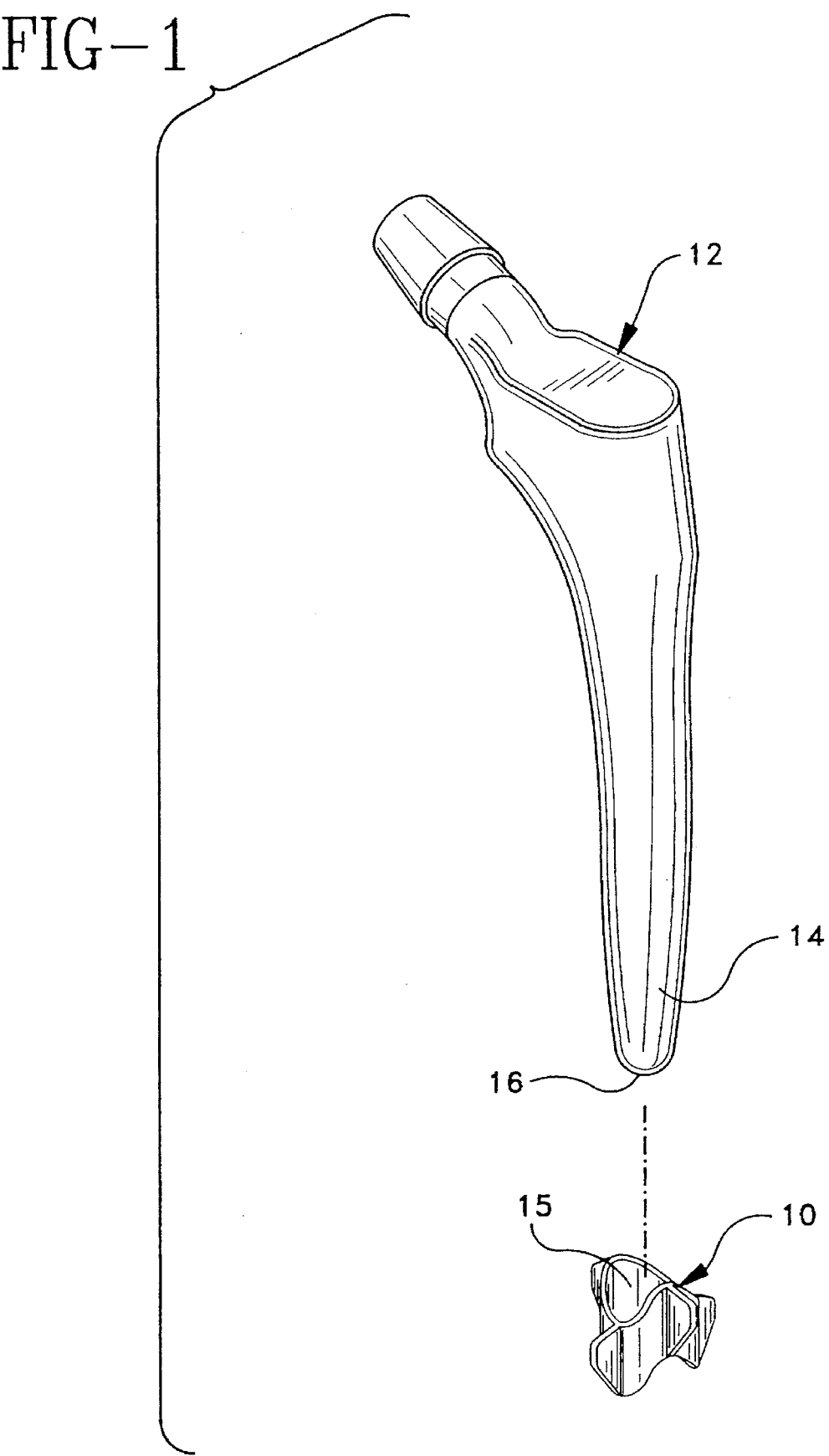
FIG. 1 is an exploded view showing a femoral implant and the centralizer of the present invention.

Referring to FIG. 1 there is shown a femoral component, by way of example of an implant stem, and a centralizer of the present invention generally denoted as 10. In the preferred embodiment, femoral component 12 has a tapered distal section 14 ending in tip 16. Section 14 is adapted to mate with a tapered inner surface 15 of the centralizer 10.

Figure 2:
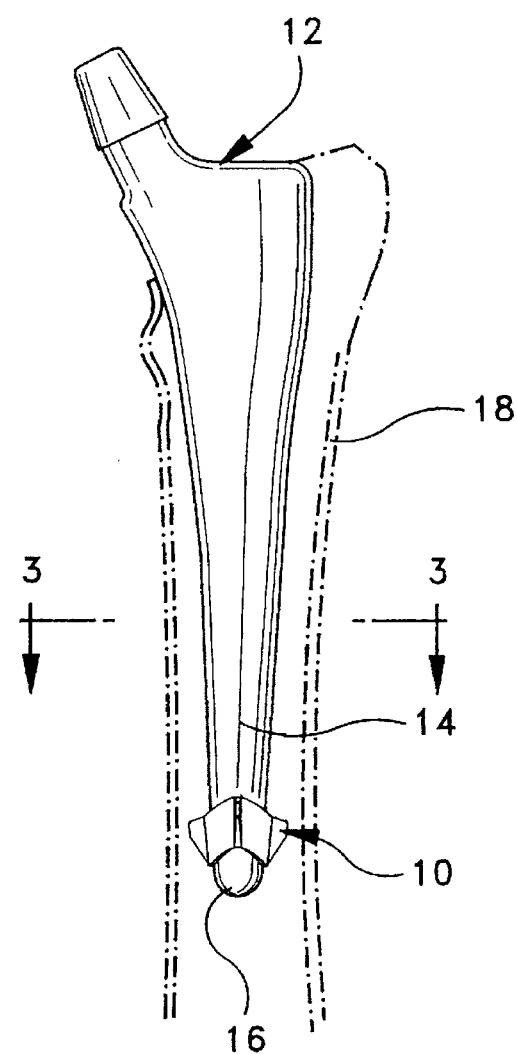
FIG. 2 is the implant and centralizer FIG. 1 in assembled position located within a femur shown in phantom.

Referring to FIG. 2 there is shown centralizer 10 mounted on distal end 14 of femoral component 12. This is accomplished by sliding the inner surface 15 of centralizer 10 over distal tip 16 of femoral component 12 until the matching tapers interlock. FIG. 2 also shows, in phantom, a femur 18. Normally the medullary canal of the femur would be reamed or otherwise prepared to receive the femoral component that would be implanted with PMMA bone cement.

Figure 3:
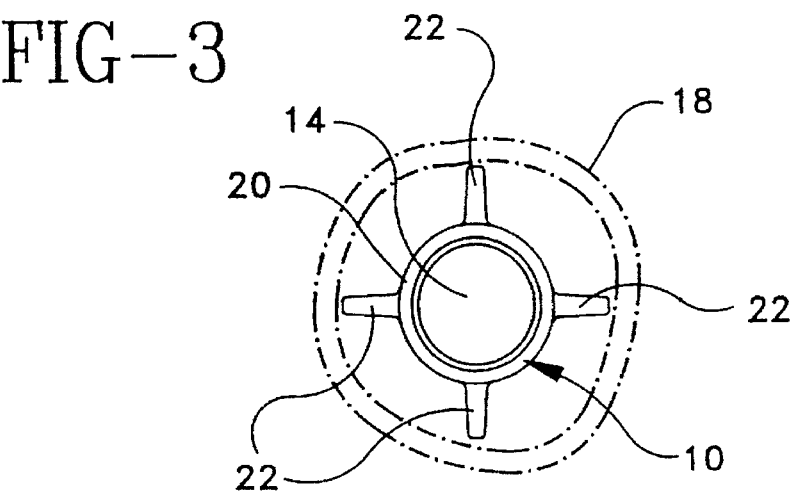
FIG. 3 is a plan view of the implant shown in FIG. 2 along lines 2—2 thereof.

Referring to FIG. 3 there is shown a cross-sectional view of centralizer 10 immediately proximal of the distal location of the centralizer on distal stem 14. While the distal stem 14 is shown as circular, it could easily be rectangular with four tapered sides with centralizer 10 also having a rectangular inner cross-section. In the preferred embodiment, centralizer 10 has a ring-like annular body 20 formed in shape to the distal stem 14. In the preferred embodiment, the centralizer body 20 has four fins 22 extending radially outwardly therefrom. A three fin or greater than four fin design is also possible.

Figure 4:
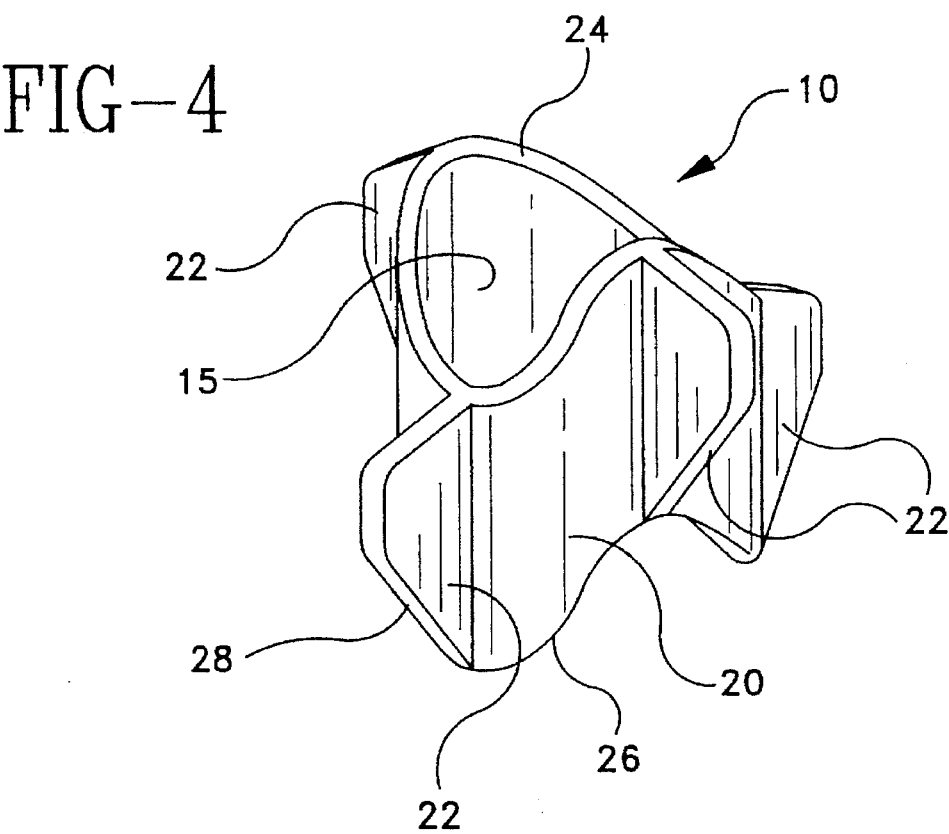
FIG. 4 is an isometric view of the centralizer of the present invention.
Figure 5:
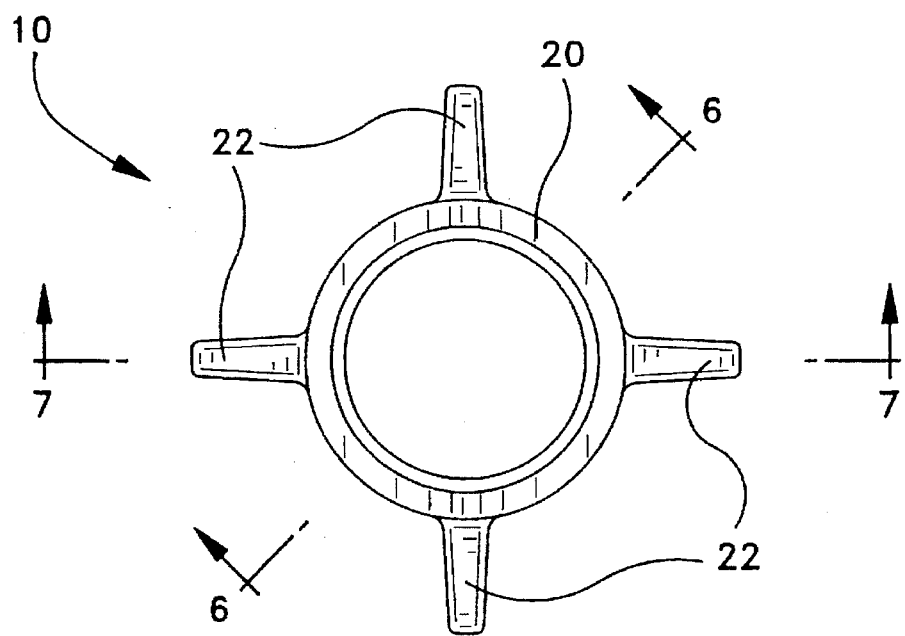
FIG. 5 is a top view of the centralizer shown in FIG. 4.
Figure 6:
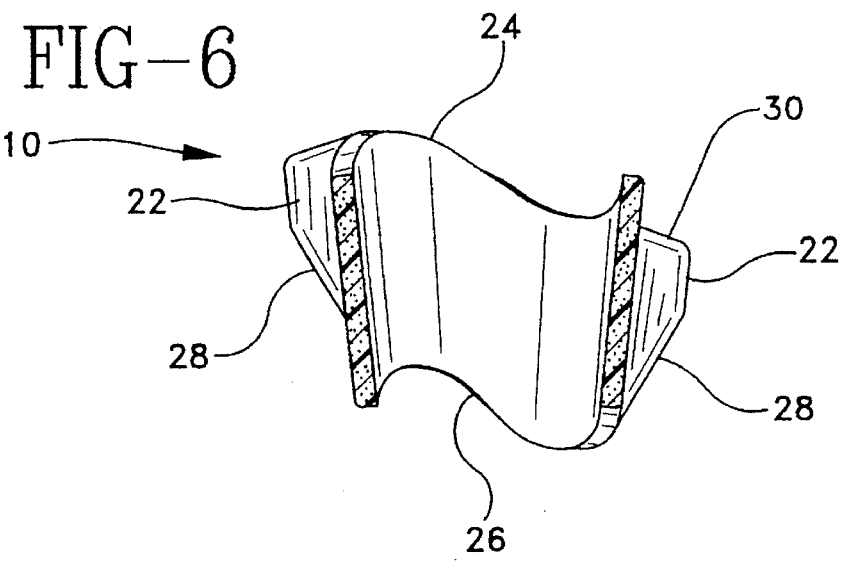
FIG. 6 is a cross-sectional elevational view of the centralizer shown in FIG. 5 along lines 6—6.
Figure 7:
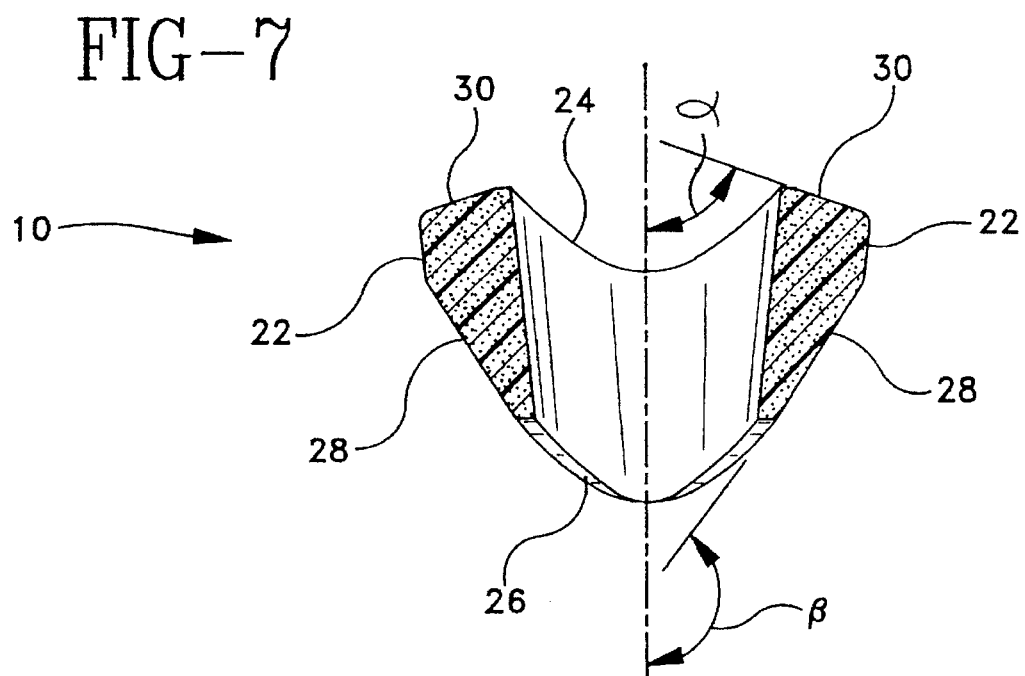
FIG. 7 is a cross-sectional elevational view of the centralizer of FIG. 5 along lines 7—7.
Figure 8:
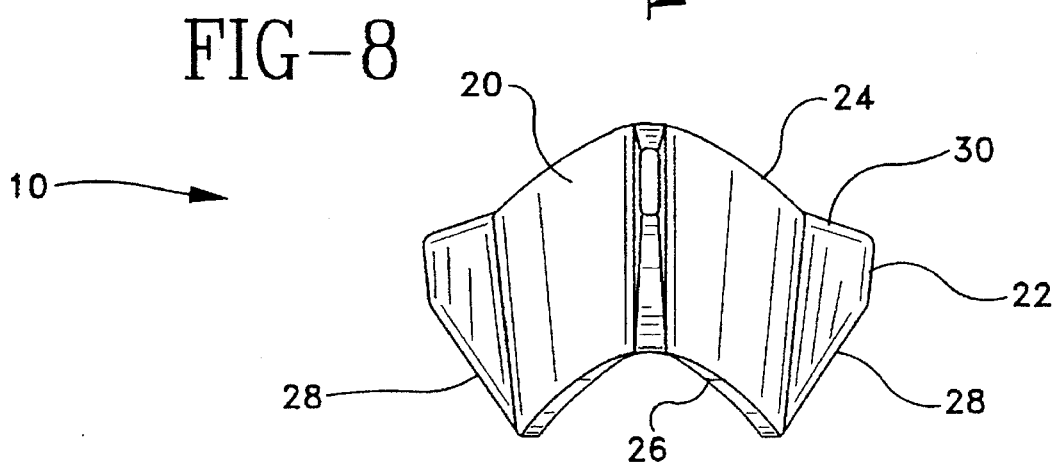
FIG. 8 is an elevation view of the centralizer shown in FIG. 4.

Referring to FIG. 3 there is shown annular body 20 of centralizer 10 with a proximal end surface 24 and a distal end surface 26. In the preferred embodiment the distance from the proximal end surface 24 and the distal end surface 26 is constant and being about 10 mm or less. As can be seen in FIGS. 4 and 6, adjacent fins 22 are offset in the proximal-distal direction. Referring to FIG. 7 it can be seen that opposite fins, in the preferred embodiment, are located on the same proximal-distal location. Alternatively, all four fins could be in different proximal-distal locations.

Again referring to FIGS. 4 through 8, it can be seen in the preferred embodiment that the leading edge 28, i.e.. distal edge, of each fin 22 forms an angle of β of greater than 135° with the body 20 of centralizer 10. In addition, the trailing edge in the preferred embodiment, i.e.., the proximal edge 30 of each fin 22, forms an angle ∝ of less than 90° with body 20.

The centralizer of the present. invention is preferably formed by injection molding polymethylmethacrylate polymer, which polymer is identical to that of the bone cement composition placed within the bone canal. This composition may be the same as that used by Howmedica Inc. in the Simplex P® bone cement material which is commercially available. As stated, the preferred method of manufacturing the centralizer is to injection mold the same within a metal mold machined to have the features of the desired centralizers. A series of molds would be utilized to form centralizers having a variety of dimensions for use with a range of implants and canal diameters. The location of the centralizer fins and their shape are first machined in metal and then the PMMA is injected at a temperature above its melting point.

While several examples of the present invention have been described, it is obvious that many changes and modifications may be made thereunto, without departing from the spirit and scope of the invention.

We claim:

1. A centralizer for the stem of a prosthetic orthopedic implant adapted for implantation into a medullary canal of a bone, said centralizer comprising:

a hollow annular body having an interior surface sized to receive the stem of the implant; and at least four fins spaced around an exterior surface of said annular body, said fins extending outwardly from said surface in a direction generally perpendicular to a longitudinal axis extending along the stem in a proximal-distal direction, each of said fins lying in a plane parallel to said longitudinal axis of said stem, each of said fins being offset from neighboring fins in said proximal-distal direction.

2. The centralizer as set forth in claim 1 wherein said fins are equally spaced around said annular body.

3. The centralizer as set forth in claim 1 wherein said annular body has proximal and a distal end surfaces spaced a predetermined distance apart, said fins having a base adjacent said annular body extending over a substantial portion of said predetermined distance, said end surfaces undulating in a manner to compensate for said offset of said neighboring fins in said proximal distal direction to maintain said predetermined distance generally constant around said annular body.

4. The centralizer of claim 3 wherein said fins are equally spaced around said annular body.

5. The centralizer of claim 4 having four fins, wherein opposite fins of said four fins are located at the same proximal-distal location on said annular body.

6. The centralizer of claim 3 wherein the length of said fins in the proximal-distal direction decreases on moving outwardly in a direction generally perpendicular to said longitudinal axis.

7. The centralizer of claim 1 wherein said interior surface of said annular body is tapered inwardly towards said longitudinal axis of said stem in the proximal-distal direction.

8. The centralizer of claim 1 wherein said centralizer is made of polymethylmethacrylate.

9. An orthopedic implant for implantation into the medullary canal of a bone comprising:

a stem for implantation into said medullary canal;

a centralizer removably engaging an end of said stem, said centralizer having a hollow annular body having an interior surface for engaging said stem, said centralizer having a plurality of fins extending outwardly from an exterior surface thereof in a direction generally perpendicular to a longitudinal axis extending along said stem in a proximal-distal direction, each of said fins lying in a plane parallel to said longitudinal axis of said stem, each of said fins being offset from neighboring fins in a proximal-distal direction.

10. The centralizer as set forth in claim 9 wherein said fins are equally spaced around said annular body.

11. The centralizer as set forth in claim 9 wherein said annular body has proximal and a distal end surfaces spaced a predetermined distance apart, said fins having a base adjacent said annular body extending over a substantial portion of said predetermined distance, said end surfaces undulating in a manner to compensate for said offset of said neighboring fins in said proximal distal direction to maintain said predetermined distance generally constant around said annular body.

12. The centralizer of claim 11 wherein said fins are equally spaced around said annular body.

13. The centralizer of claim 12 having four fins, wherein opposite fins of said four fins are located at the same proximal-distal location on said annular body.

14. The centralizer of claim 11 wherein the length of said fins in the proximal-distal direction decreases on moving outwardly in a direction generally perpendicular to said longitudinal axis.

15. The centralizer of claim 9 wherein said interior surface of said annular body is tapered inwardly towards said longitudinal axis of said stem in the proximal-distal direction.

16. A centralizer for the stem of an orthopedic implant comprising:

a hollow annular body having an interior surface sized to engage the stem of the implant, said centralizer having a plurality of fins extending outwardly from an exterior surface thereof in a direction generally perpendicular to a longitudinal axis extending along said stem in a proximal-distal direction, each of said fins lying in a plane parallel to said longitudinal axis of said stem, at least one of said fins being offset from said neighboring fins in a proximal-distal direction.

17. The centralizer of claim 16 wherein said fins are equally spaced around said annular body.

18. The centralizer as set forth in claim 17 wherein said annular body has proximal and a distal end surfaces spaced a predetermined distance apart, said fins having a base adjacent said annular body extending over a substantial portion of said predetermined distance, said end surfaces undulating in a manner to compensate for said offset of said neighboring fins in said proximal distal direction to maintain said predetermined distance generally constant around said annular body.

19. The centralizer of claim 18 having four fins, wherein opposite fins of said four fins are located at the same proximal-distal location on said annular body.

20. The centralizer of claim 19 wherein said interior surface of said annular body is tapered inwardly toward said longitudinal axis of said stem in the proximal-distal direction.

* * * * *